United States Patent
Flohe et al.

(10) Patent No.: US 6,884,601 B1
(45) Date of Patent: Apr. 26, 2005

(54) METHOD TO DETECT FERTILIZATION POTENTIAL OF SPERM

(75) Inventors: Leopold Flohe, Mascheroder Weg 1, D-38124 Braunschweig (DE); Fulvio Ursini, Braunschweig (DE); Antonella Roveri, Braunschweig (DE)

(73) Assignee: Leopold Flohe, Braunschweig (DE)

( * ) Notice: Subject to any disclaimer, the term of this patent is extended or adjusted under 35 U.S.C. 154(b) by 0 days.

(21) Appl. No.: 09/913,361

(22) PCT Filed: Mar. 6, 2000

(86) PCT No.: PCT/EP00/01877

§ 371 (c)(1), (2), (4) Date: Dec. 3, 2001

(87) PCT Pub. No.: WO00/54054

PCT Pub. Date: Sep. 14, 2000

(30) Foreign Application Priority Data

Mar. 9, 1999  (EP) ............................. 99103959

(51) Int. Cl.⁷ ................................................ C12Q 1/28
(52) U.S. Cl. ............................. 435/28; 435/2; 435/806
(58) Field of Search ........................... 435/28, 806, 2, 435/29; 424/561; 436/906

(56) References Cited

U.S. PATENT DOCUMENTS 5,895,749 A * 4/1999 Alvarez ........................ 435/7.4
6,231,853 B1 * 5/2001 Hillman et al. ............. 424/94.4

FOREIGN PATENT DOCUMENTS

WO    WO 96/13225    *  5/1996

OTHER PUBLICATIONS

Maiorino M. Testosterone Mediates Expression of the Selenoprotein PHGPx . . . The FASEB J, vol. 12, 1359–1170, 1998.*
Ursini F. Dual Function of the Selenoprotein PHGPx During Sperm Maturation. Science 285 1393–1396, 1999.*
Maurer S. Attempt to Differentiate Between Individual Glutathione Peroxidases in Biological Samples. Z Ernahrungswiss 37 Supp 1, 110–113, 1998.*
Roveri A. Enzymatic and Immunological Measurements of Soluble and Membrane Bound PHGP. Methods in Enzymology 233, 202–212, 1994.*
Maiorino M. Phospholipid Hydroperoxide Glutathione Peroxidase. Methods in Enzymology 184, 448–457, 1990.*
Roveri A. Purification and Characterization of Phospholipid Hydroperoxide Glutathione Peroxidase from Rat Testis Mitochondrial Membranes. Biochimica et Biophysica acta 1208(2)211–221, 1994.*
Godeas C. Distribution and Possible Novel Role of Phospholipid Hydroperoxide Glutathione Peroixdase in Rat Epidiymal Spermatozoa. Biology of Reproduction 57(6)1502–1508, 1997.*

* cited by examiner

*Primary Examiner*—Ralph Gitomer
(74) *Attorney, Agent, or Firm*—Frommer Lawrence & Haug LLP; Ronald R. Santucci

(57) ABSTRACT

The invention relates to a method to detect male antifertility problems based on the determination of latent phospholipid hydroperoxide glutathione peroxidase (PHGPx).

7 Claims, 4 Drawing Sheets

METHOD TO DETECT FERTILIZATION POTENTIAL OF SPERM

This application is a National Stage Application filed under 371 from International Application No. PCT/EP00/01877 filed Mar. 6, 2000, which is a continuation of Application EP 00 103 959.5 filed Mar. 9, 1999.

FIELD OF THE INVENTION

The invention relates to a method to detect male antifertility problems based on the determination of latent phospholipid hydroperoxide glutathione peroxidase (PHGPx).

Selenium is essential for male fertility. In mature mammalian spermatozoa it is largely restricted to the midpiece harbouring the helix of mitochondria embedded into a keratine-like selenium-enriched matrix called the mitochondrial capsule. Selenium deficiency is associated with impaired sperm motility, structural alterations of the midpiece up to breakages, and loss of flagellum. The predominant selenoprotein of the mammalian male reproductive system, phospholipid hydroperoxide glutathione peroxidase (PHGPx), was shown to be preferentially expressed in round spermatids but was hardly detectable in terms of messenger RNA or activity in spermatozoa. The basis of the invention is the discovery that PHGPx persists in spermatozoa but as insoluble, enzymatically inactive material forming the mitochondrial capsule. PHGPx activity of this material can be restored by high concentrations of thiols. PHGPx, thus, acts as a peroxidase in the proliferating germ epithelium to prevent oxidative damage. In the late stages of sperm maturation it is oxidatively cross-linked to become a structural element indispensible for sperm function. Accordingly, the determination of the PHGPx content in sperm or any other tissue of humans or livestock can be used to estimate the fertilization potential of sperm.

SUMMARY OF THE INVENTION

The invention thus in accordance with claim 1 provides a method for the determination of latent phospholipid hydroperoxide glutathione peroxidase (PHGPx) comprising the steps of
a) obtaining a sperm sample,
b) solubilizing the spermatozoa by using detergents and chaotropic agents and reactivating latent PHGPx by using high concentrations of thiols and
c) determining enzymatic activity of reactivated latent PHGPx.

In a further aspect the invention relates to the use of the inventive method in a method for predicting the fertilizing potential of spermatozoa in sperm samples.

Further advantageous and/or preferred embodiments of the invention are subject-matter of the subclaims.

In a preferred embodiment of the inventive method an additional step of removing any reactivating reagents by, e.g., gel filtration is provided between the step of solubilizing the spermatozoa and the step of determining the enzymatic activity of reactivated latent PHGPx.

In a further embodiment of the invention instead of determining enzymatic activity of reactivated latent PHGPx the content of solubilized PHGPx is determined by conventional immunological techniques or measurement of enzymatic activity.

The used chaotropic a gent is, for example, 4–8 M guanidine chloride, 4–8 M guanidine thiocyanate or 5–8 M urea.

The used thiol is, for example, 50–300 mM 2-mercaptoethanol, 25–300 mM dithiothreitol (DTT) or dithio-erythritol (DTE).

The sperm sample is, for example, from humans or livestock.

EXAMPLES

In the following the invention is disclosed in more detail with reference to examples and to drawings. However, the described specific forms or preferred embodiments are to be considered in all respects as illustrative and not restrictive, the scope of the invention being indicated by the appended claims rather than by the following description, and all changes which come within the meaning and range of equivalency of the claims are therefore intended to be embraced therein.

Regarding the cited literature a reference list with more detailed bibliographic information can be found at the end of this specification.

Routine preparations of rat sperm mitochondrial capsules (1) yielded a fraction which was insoluble in 1% SDS and 0.2 mM DTT and displayed expected vesicular appearance in electron microscopy (FIG. 1a). The vesicles readily disintegrated upon exposure to 0.1 M mercaptoethanol (FIG. 1b) and became fully soluble in 6 M guanidine-HCL. When the solubilized capsule material was subjected to gel electrophoresis essentially four bands in the 20 kDa region were detected (FIG. 1 c, left lane). Western blotting revealed that the most prominent one reacted with antibodies directed against PHGPx (FIG. 1c, right lane) which is undetectable as active peroxidase in mature spermatozoa (Tab. 1). Also, N-terminal sequencing of the 21 kDa band representing about 46% of total protein content according to Coomassie stain revealed that it consisted of at least 95% pure PHGPx. Puzzled by this unexpected to finding, we investigated the composition of the mitochondrial capsules in more detail by 2D-electrophoresis (FIG. 2a) followed by microsequencing and/or MALDI-TOF for identification (FIG. 2b). For this purpose the capsules were dissolved completely in a buffer designed for electrophoretic separation of membrane proteins (see Methods). The spot migrating with an apparent molecular weight of about 21 kDa and focussing at a pH near 8 (spot 3) proved to be PHGPx according to the masses of tryptic peptides detected by MALDI-TOF (FIG. 2b). By the same technique, also the slightly more acidic charge isomer (spot 4), the more basic ones (spots 1, 2 and 5) as well as the spots 6 and 7 exhibiting a smaller apparent molecular mass were shown to contain PHGPx (FIG. 2c). The predicted N-terminal (pos. 3–12) and C-terminal peptides (pos. 165–170), the fragment corresponding to positions 100–105 and those expected from the basic sequence part 119–151 were too small to be reliably identified. Interestingly, the fragment corresponding to positions 34–48 comprising the active site selenocysteine was not detected either. With these exceptions, however, the MALDI-TOF spectra unequivocally complied with the PHGPx sequence and thus proved the presence of PHGPx in spots 1–7. On a thicker 2D-gel developed with a non-linear gradient from pH 3–10 also five distinct spots were detected in the 20 kDa region. In this experiments the presence of PHGPx was verified by microsequencing of major tryptic peptides (not shown). Again the spots representing PHGPx were the most prominent ones present in the gel.

The spots 1–6 of FIG. 2a proved to be essentially homogeneous. As is exemplified in FIG. 2b, the fragments yielding MALDI-TOF signals of significant intensities could be attributed to PHGPx. Only in the minor spot 7 a trace of impurity was detected, which was tentatively identified as a subunit of the T cell receptor variable region (acc. no.

228109). Based on integrated stain intensities of the individual spots those representing PHGPx amounted to about 50% of the capsule material. Most of the minor components (see FIG. 2a) are not likely constituents of the capsule, which is believed to be built up by apposition of extramitochondrial proteins onto the outer mitochondrial membrane. In other gels further proteins like the mitochondrial glutathione S-transferase subunit Yb-2 (acc. no. 121719) and an endothelin converting enzyme (acc. no. 1706564) could be identified by MALDI-TOF or micro-sequencing (not shown). Spots 8 and 9 were identified as the "outer dense fiber protein", a cystine-rich structural sperm protein, which is associated with the helix of mitochondria in the sperm midpiece but also extends into the flagellum (7). In view of the nature of the additional proteins detected, the PHGPx content of the actual mitochondrial capsule should substantially exceed the 50% observed by gel scanning.

Despite intense search, we could not detect any trace of the "sperm mitochondria-associated cysteine-rich protein ("SMCP") (7) in our capsule preparation. This cysteine- and proline-rich protein had for long been considered the selenoprotein accounting for the selenium content of the mitochondrial capsule in sperm (1,8,9). Cloning of the rat SMCP gene, however, revealed that it did not contain any in-frame TGA codon enabling selenocysteine incorporation (10). In mice, the three in-frame TGA codons proved to be upstream of the translation start (7). In developing mouse sperm SMCP stayed cytosolic up to states in which the mitochondrial capsule was already formed and only became superficially associated with the outer mitochondrial membranes of late spermatids and epididymal spermatozoa (7). SMCP thus is not necessarily an integral part of the mitochondrial capsule nor it is a selenoprotein. Instead, the "mitochondrial capsule selenoprotein (MCS)", as SMCP was originally referred to (1,7–10), is indeed PHGPx.

The chemical modifications of PHGPx leading to distinct differences in charge and apparent MW could not be reliably elucidated. Sequencing revealed an identical N-terminus of the size isomers starting with ASRDDWRCAR, i.e. a sequence either corresponging to the originally proposed translation start (11) after cleavage of the first two residues or derived from a possible pre-PHGPx (12) after processing of a mitochondrial leader peptide (13). Tryptic fragments extending towards the C-terminus up to position 164 were consistently observed also with the faster migrating specimen (FIG. 2c) which leaves little room to explain an apparent MW difference of 1 to 1.5 kDa. As to the charge isomers, it may be recalled that a potential phophorylation had been inferred from early attempts to sequence pig heart PHGPx (14). The assignment of masses to possibly phosphorylated tryptic peptides, however, remained equivocal. Certainly, more trivial events such as deaminations of Gln and Asn residues, C-terminal degradation, oxidation of the active site selenium, or its elimination might have contributed to the charge heterogeneity.

DETAILED DESCRIPTION OF THE INVENTION

PHGPx as the major component of the sperm mitochondrial capsule had so far escaped attention, since as such it is enzymatically inactive, as it generally is in mature spermatozoa prepared from the tail of the epididymis (Tab. 1). It is neither reactivated by glutathione in the low millimolar range as used under conventional test conditions. High concentrations of thiols (0.1 M 2-mercaptoethanol or dithiothreitol), which in the presence of guanidine fully dissolve the capsule, regenerate a significant PHGPx activity, as measured after elimination of denaturating and reducing agents (Tab. 1). In fact, the specific activities thus obtained from mitochondrial capsules exceed, by a factor of 20, the highest values ever measured, i.e. in spermatogenic cells. Nevertheless, this extreme PHGPx activity is still low compared to its content in PHGPx protein. Based on the specific activity of pure PHGPx, the reactivated enzyme would be equivalent to less than 3% of the capsule protein, whereas the 2D-electrophoresis suggests a PHGPx protein content of at least 50%. It is worth noting that the same reductive procedure does not increase the specific activity of PHGPx in spermatogenic cells from testicular tubules (Tab. 1). The switch of PHGPx from a soluble active enzyme to an enzymatically inactive structural protein thus occurs during final differentiation of spermatozoa.

The alternate roles of PHGPx, being either a glutathione-dependent hydroperoxide reductase or a structural protein, are not necessarily unrelated. One of the features common to all glutathione peroxidases is a selenocysteine residue which together with a tryptophan and a glutamine residue forms a catalytic triad (15,16). Therein the selenol group of the selenocysteine residue is dissociated and highly activated by hydrogen bonding to reduce hydroperoxides with high rate constants. The reaction product, a selenenic acid derivative, R-SeOH, will readily react with thiols, e.g. GSH, to form an intermediate with a selenadisulfide bridge between enzyme and substrate, R-Se-S-G, from which the ground state enzyme can be regenerated by a second GSH. PHGPx is unique among the glutathione peroxidases in several respects: i) It usually is monomeric having its active site freely accessible at the surface; this facilitates interaction with bulky substrates. ii) Arginine residues surrounding the active site and specifically binding glutathione in most types of glutathione peroxidases are lacking in PHGPx (16); correspondingly, its specificity for the reducing substrate is less pronounced (16). It therefore can be envisaged that oxidized PHGPx may form diselenide or selenadisulfide bridges with exposed SeH or SH groups of proteins (16) including PHGPx itself, and this process, possibly followed by SE/SS, SH/SeS, or SH/SeSe exchange reactions, will create cross-linked protein aggregates. This ability of PHGPx might become particularly important if cells are exposed to hydroperoxides at extremely low concentration of glutathione, as is documented for late states of spermatogenesis (17–20). FIG. 3 is to mimick the oxidative events occurring during sperm maturation. Short term exposure of soluble proteins derived from spermatogenic cells to moderate $H_2O_2$ concentrations in the absence of GSH yields a variety of PHGPx-containing high molecular weight aggregates. Undoubtedly, therefore, PHGPx, by means of its intrinsic enzymatic potential, can catalyse oxidative protein aggregation using protein thiols as alternate substrates. During sperm maturation, PHGPx thereby transforms itself into an enzymatically inactivated structural protein. This view, however, is not to imply that PHGPx could not depend on additional proteins when building up the highly organized architecture of the spermatozoal midpiece.

Our findings require a fundamental reconsideration of the role of selenium in male fertilty. The intriguing predominance of the selenoprotein PHGPx in the male reproductive system has so far been believed to reflect the necessity to shield germ line cells from oxidative damage by hydroperoxides and reactive oxygen species derived therefrom (11, 17,21,22). This concept still merits attention with regard to the mutagenic potential of hydroperoxides and probably holds true for the early phases of spermatogenesis where PHGPx is still present as an active peroxidase (6,21). At this stage related activities reported for PHGPx or other glutathione peroxidases, e.g. silencing lipoxygenases (23), dampening the activation of NF B (24) or inhibiting apoptosis (25), may also be relevant. In later stages of spermatogenesis characterized by a shift of the redox status resulting in loss of GSH (18–20,26), the ability of PHGPx to use protein thiols as alternate substrates opens up new perspectives of redox regulation which remain to be explored. In the mature spermatozoon PHGPx has experienced a pronounced metamorphosis now being a major constituent of the keratinuous material embedding the mitochondrial helix. It appears revealing that precisely this architectural pecularity in the midpiece of spermatozoa shows gross structural alterations in selenium deficiency. We therefore assume that the mechanical instability of the midpiece observed in selenium deficiency is a consequence of an impaired PHGPx biosynthesis. This view implies that it is not the antioxidant capacity of PHGPx which is crucial for male fertility but its ability to utilize hydroperoxides to build an indispensable structural element of the spermatozoon.

Any shortage of PHGPx during sperm maturation, be it due to selenium deficiency, other reasons of inhibited biosynthesis or inhibition of activity should therefore result in disturbed sperm midpiece architecture and, in consequence, loss of fertilization potential of sperm. This conclusion was further corroborated by determination of reactivated PHGPx in sperm of individuals with documented fertility problems. The latter were divided into three groups: depending on whether i) intrauterine sperm injection (iui) or ii) conventional in-vitro-fertilisation (ivt-et) was still successful or iii) intracytoplasmatic sperm injection was required (icsi). As shown in FIG. 4, the PHGPx values differed markedly between these groups. While the iui group displayed values close to normal, PHGPx in the icsi group was almost absent, the ivf-et group ranking in between. The reasons of the diverse PHGPx content being unknown, the data reveal that markedly reduced PHGPx content in sperm is incompatible with normal male fertility. Similarly, there is a strong correlation between "typical" sperm appearance (FIG. 5) and "fast" moving sperm with PHGPx content (FIG. 6). This correlation, however, shows marked scattering of data indicating that PHGPx content of sperm is not the only reason of abnormal shape and motillity of sperm. It should also be pointed out that the sperm samples were taken from individuals without any obvious disease suggesting that extremely reduced PHGPx levels are well tolerated.

Taken together, the ovseration that PHGPx builds up an esssential structure of sperm and that its content in sperm correlates with the fertilization potential leads to the inventive concept to use the PHGPx content of sperm as a predictive parameter for the necessary measures to overcome male fertility problems. To this end, it appears necessary to reactivate the PHGPx contained in sperm in order to estimate its content by either immunological methods or by any of the established determinations of its specific activity. (28, 29).

Methods

Preparation of Rat Spermatozoa, Tubular Cells and Mitochondrial Capsule

Spermatozoa of four month old Wistar rats (about 300 grams of body weight) were collected by squeezing cauda epididymis and vas deferens in phosphate buffer saline (PBS) and by centrifugating at 600×g for 10 minutes. Cell and sperm pellets were layered on a discontinous 45%, 70% and 95% Percoll gradient and centrifugated at 300×g for 20 min. Spermatogenic cells stacked on top of the gradient, while spermatozoa separated into the 70% Percoll layer.

Cells from seminiferous epithelium were prepared as follows (26): testes were deprived of albuginea, seminiferous tubules were cut into small pieces in PBS containing 0.250 mg/ml collagenase, and incubated twice 25° C. for 15 min. Cells then were filtered through a stainless steel screen (140 μm pore), washed in PBS and centrifugated at 300×g for 10 min. Sperm mitochondrial capsule was prepared according to Calvin et al. (1): sperms were resuspended in 0.05 M Tris-HCl pH 8.0 at the concentration of $10^6$ cells/ml and treated with trypsin (0.2 mg/ml) for 10 minutes. After stopping the protease action with trypsin inhibitor (0.5 mg/ml) and SDS (10 mg/ml) sperms were centrifugated at 1,500×g for 10 minutes. Pellets were resuspended in 0.05 M Tris-HCl, pH 8.5 containing 1% sodium dodecyl sulphate (SDS), and 0.2 mM DTT and kept under continuous stirring for 30 minutes. Following centrifugation at 4,500×g for 15 min, the resulting supernatant was layered on a 1.6 M sucrose cushion. After centrifugation for 20 min at 18,000×g in a swinging rotor, sperm capsules were collected as a band at the top of the sucrose cushion, washed in Tris-HCl, pH 8.0 and spun at 140,000×g.

1D-Electrophoresis and Western Blotting

Electrophoresis was performed according to Laemmli under either reducing (+2-mercaptoethanol) or non-reducing conditions. Proteins were blotted onto nitrocellulose, probed with an antigen-purified rabbit antibody raised against pig heart PHGPx and detected by biotinylated anti rabbit IgG and streptoavidin alkaline phosphatase complex.

2D-Electrophoresis

100 μg of the mitochondrial capsule material was dissolved in 400 μl of a solution containing of 7 M urea, 2 M thiourea, 4% CHAPS, 40 mM DTT, 20 mM Tris base and 0.5% IPG buffer (Pharmacia) and focused in an IPG-phor (Pharmacia) 2-D gel electrophoresis system at 20° C. by stepwise increasing voltage up to 5000 V but not exceeding a current of 30 μA per IPG strip. The pH gradient was non-linear from 3–10 or linear from 3–10 or 6–11. The focused IPG strips were then equilibrated for SDS electrophoresis (10 min each) with a solution containing 60 mM DTT in 6 M urea, 30% glycerol, 0.05 M Tris-HCl buffer pH 8.8 and in the same buffer where DTT was substituted by 250 mM iodoacetamide. After SDS-electrophoresis (12% polyacrylamide) the gels were stained with Coomassie.

Protein Identification

Coomassie-stained spots were cut out from the gels, neutralized with $(NH_4)HCO_3$, destained with 400 μl 50% acetonitrile/10 mM $(NH_4)HCO_3$ and dried in a Speed Vac Concentrator. Protein digestion was done overnight using 2 ng/μl sequencing grade trypsin (Promega) in 50 mM $(NH_4)HCO_3$ (Boehringer, Mannheim). The resulting peptides were extracted twice with 60% acetonitrile/40% $H_2O$/0.1% TFA. Extracts were combined and lyophilized in the Speed Vac Concentrator. Peptide digests were desalted on small RP18-columns, eluted with saturated α-hydroxy-4-cyano-cinnamic acid and loaded directly onto the MALDI target (27). Reflectron MALDI mass spectra were recorded on a Reflex™ MALDI/TOF-mass spectrometer (Bruker-Franzen-Analytik, Bremen). The ions were excellerated at 20 kV and reflected at 21.3 kV. Spectra were externally calibrated using the monoisotopic $MH^+$ion from two peptide standards. 100–200 laser shots were summed up for a single mass spectrum. Mass identification was performed with MS-Fit (http://falcon.ludwig.ucl.ac.uk/ucsfhtml/msfit.htm).

Alternatively, protein spots from 1.5 mm 2D-gels were digested with modified trypsin (Promega, sequencing grade) in 25 mM $(NH_4)HCO_3$ overnight at 37° C. The digests were extracted twice and dried as before and reconstituted in 10 µl water. Peptides were separated on a reversed-phase capillary column (0.5 mm×150 mm) with a gradient of acetonitrile in 0.1% formic acid/4 mM ammonium acetate at a flow rate of 5 µl/min and collected manually. Aliquots of 5 µl were spotted onto Biobrene-treated glass fiber filters and sequenced on an Applied Biosystems 494A sequencer with standard pulsed-liquid cycles. Before N-terminal sequencing, proteins were blotted from polyacrylamide gels onto PVDF membranes for 16 h at pH 8.3 (25 mM Tris-HCl, 192 mM glycine) and 100 mA (30 V).

When applicable, PHGPx was also identified by activity measurement according to (28) using the specific substrate phosphatidylcholine hydroperoxide.

a, Mitochondrial capsule prepared by trypsination and centrifugation according to (1) at 80,000 fold magnification.

b, The same preparation as shown in a, but after exposure to 0.1 M 2-mercaptoethanol for 15 min at 4° C. Contamination of the capsule material by mitochondria is evident from the presence of mitochondrial ghosts. c, SDS gel electrophoresis of proteins extracted from capsule material (see Methods) by treatment with 0.1 M 2-mercaptoethanol, 0.1 M Tris-HCl, pH 7.5, and 8 M guanidine HCl. Left lane is stained with Coomassie, right lane demonstrates presence of PHGPx by Western blotting.

Figure 1:
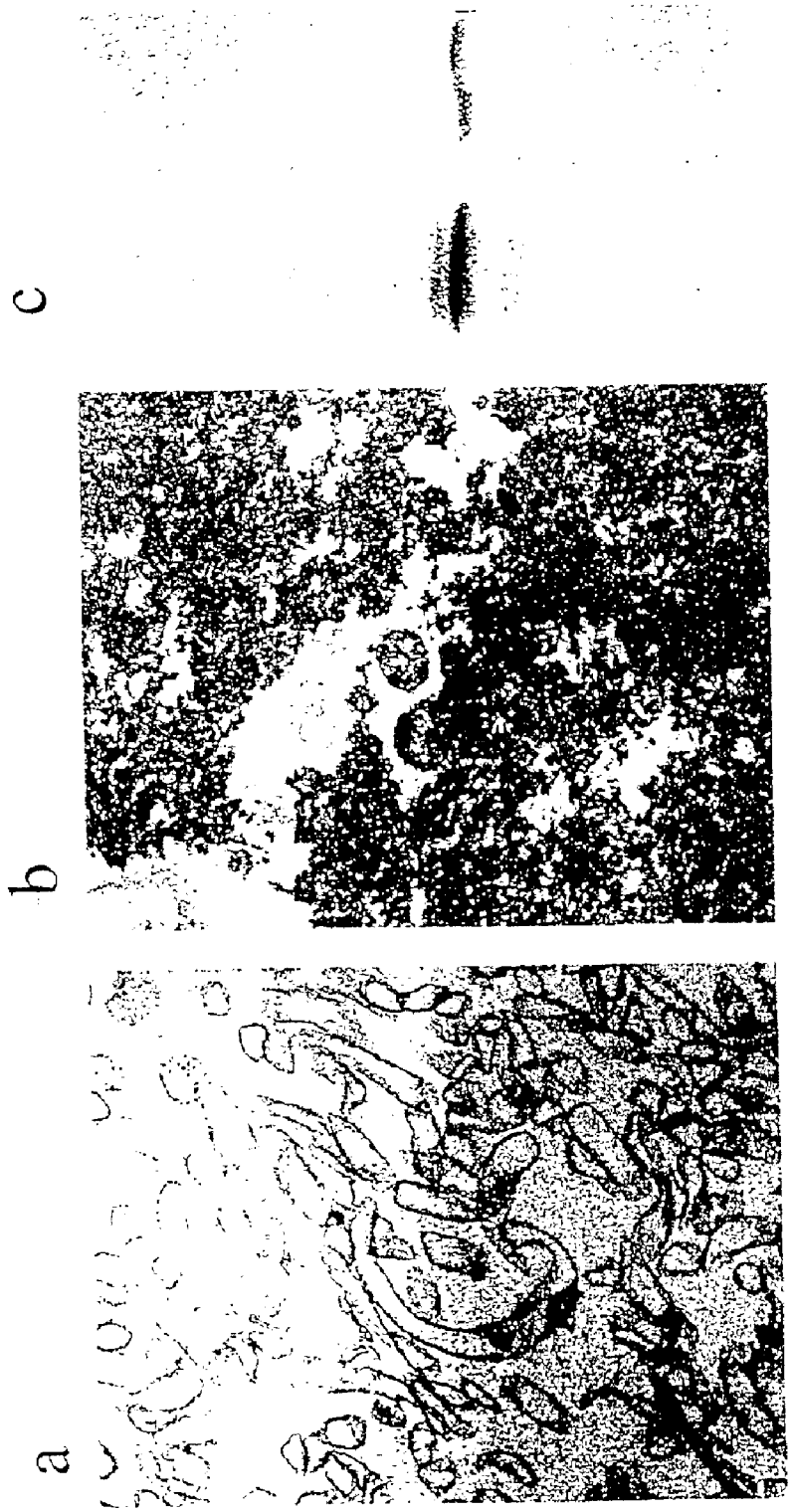
FIG. 1 Presence of PHGPx in the mitochondrial capsule of spermatozoa.
Figure 2:
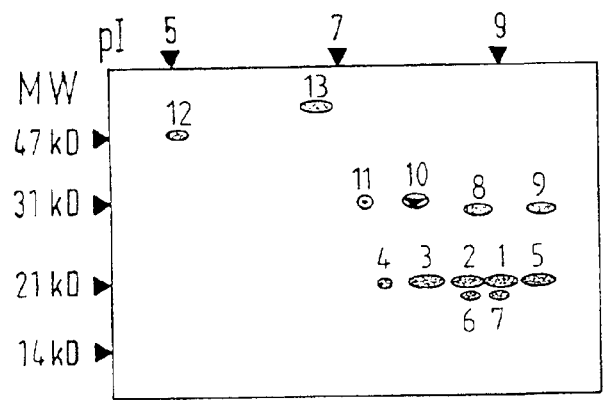
Figure 2:
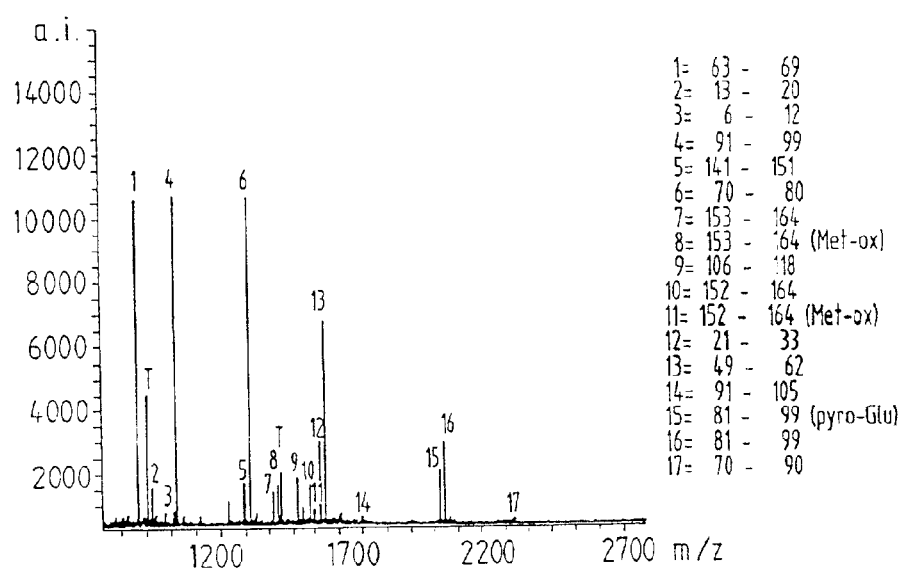

FIG. 2 showws the analysis of the composition of the mitochondrial capsule of spermatozoa a, 2D-electrophoresis of purified dissolved capsule material. Proteins were focused in a linear pH-gradient from 3 to 10 (horizontal direction), then reduced, amidocarboxymethylated, subjected to SDS-electrophoresis, and stained with Coomassie. MALDI-TOF analysis of the visible spots identified the following proteins (SwissProt data base): spot 1–7 PHGPx (MW 19 443; pI 8.27; acc. no. 544434); spots 8 and 9, outer dense fiber protein (MW 27351; pI 8.36; acc. no. P21769); spots 10 and 11, voltage-dependent anion channel-like protein (MW 31720; pI 7.44; acc. no. 540011); spot 12, "stress-activated protein kinase" (MW 48107; pI 5.65; acc. no. 493207); spot 13, glycerol-3-phosphate dehydrogenase (MW 76479; pI 5.86; acc. no. P35571).

b, MALDI-TOF spectrum (overview) of tryptic peptides obtained from PHGPx as found in spot 3. Abscissa, mass/charge ratio of the peptide fragments; ordinate, arbitrary units of intensity; numbers at mass signals, identified peptides in the PHGPx sequence (see insert for position numbers); T, trypsin-derived fragments.

c, Compilation of tryptic PHGPx fragments identified in spots 1–7 by MALDI-TOF. Vertical lines designate potential tryptic lag cleavage sites. Dark blocks, identified typical cleavage products; shadowed blocks, masses resulting from incomplete cleavage or equivocally assignable to different fragments (e.g. 3–9 and 63–69).

Figure 3:
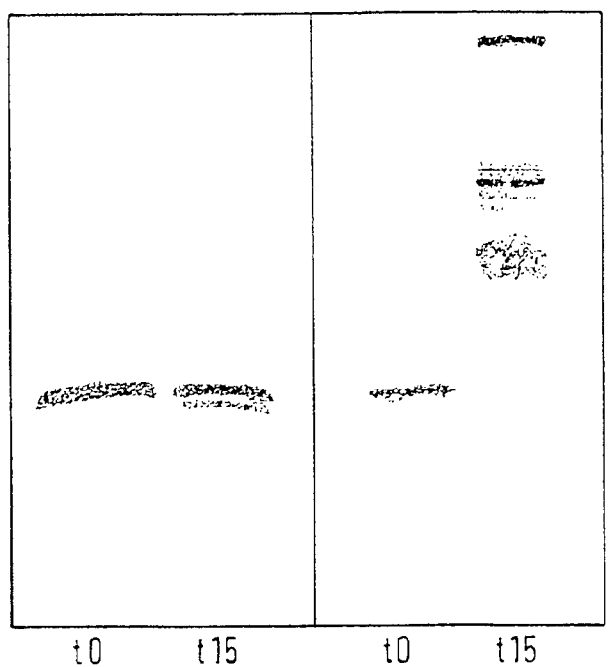

FIG. 3 shows the formation of PHGPx-containing aggregates from spermatogenetic cells by $H_2O_2$ in the absence of GSH. Spermatogenic cells were homogenised in 0.1 M Tris-HCl, 6 M guanidine-HCl, 0.5 µg/ml pepstatin A, 0.7 µg/ml leupeptin and 5 mM 2-mercaptoethanol at pH 7.5 and 4° C. After centrifugation at 105,000×g for 30 min, excess reagents were removed by gel permeation using NAP 5 columns equilibrated with 10 mM Tris-HCl, 0.15 M NaCl, 1 mM EDTA and 0.1% Triton X-100, pH 7.5. Immediately (t 0) and 15 min after (t 15) the addition of 75 µM $H_2O_2$ aliquots of the mixture (0.05 mg of protein) were withdrawn and subjected to electrophoresis under (a) reducing and (b) non reducing conditions. After blotting on nitrocellulose, PHGPx was detected by specific antibodies.

Figure 4:
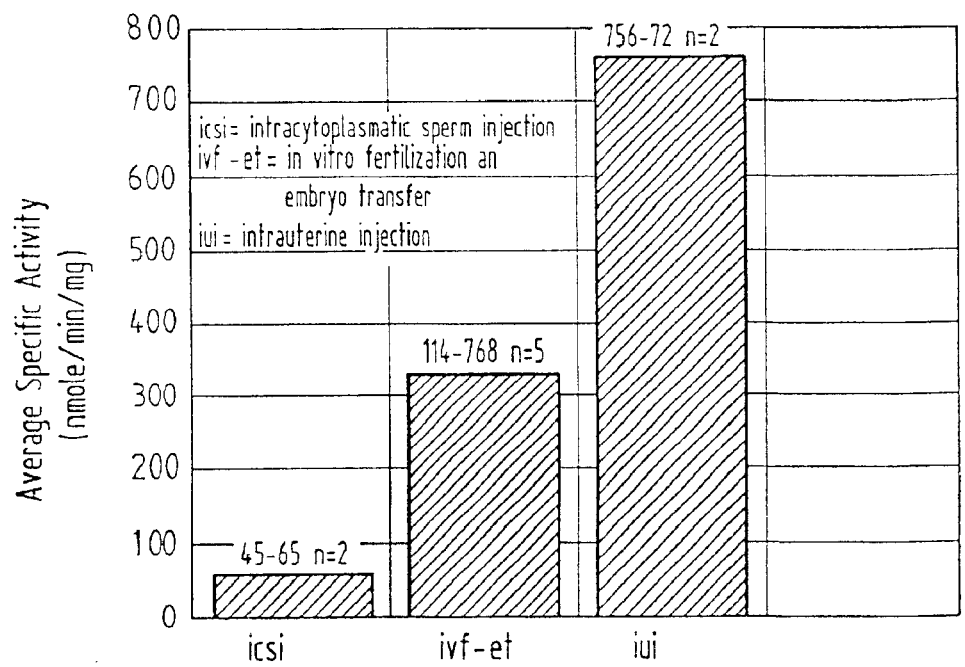

FIG. 4 shows the PHGPx specific activity in extracts (0.1% Triton X-100 and 0.1 M 2-mercaptoethanol) of human sperm. Correlation between this parameter and therapeutic appproach in cases of couple infertility.

Figure 5:
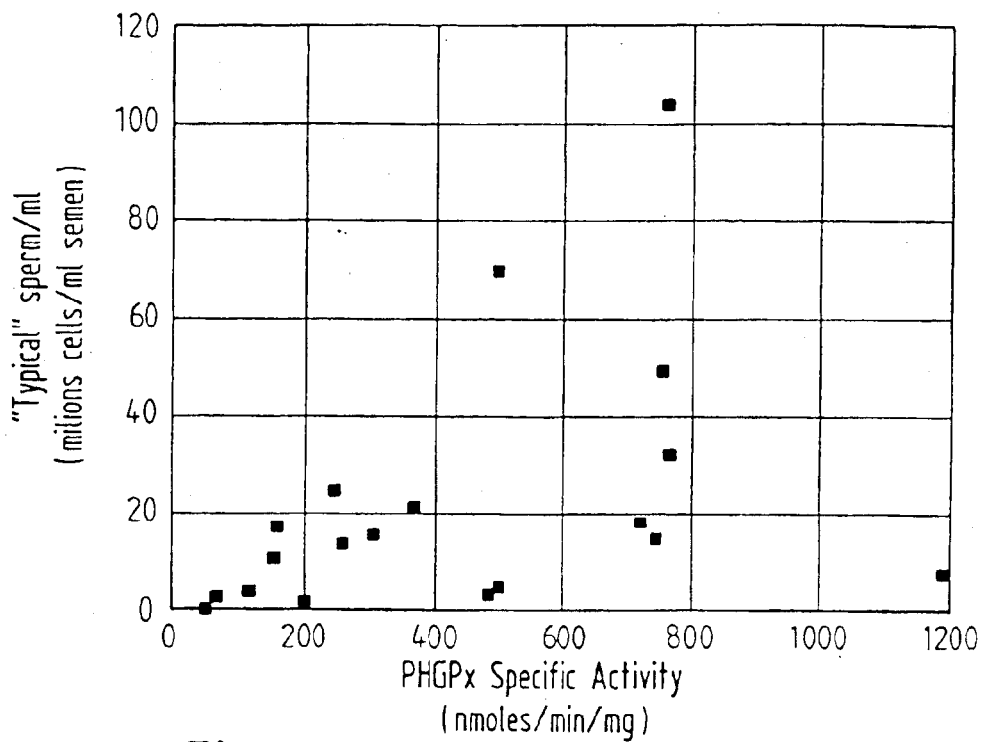

FIG. 5 shows the relationship between PHGPx specific activity and number of "typical" sperms per milliliter of semen. "Typical" is a morphological parameter of sperm evaluation.

Figure 6:
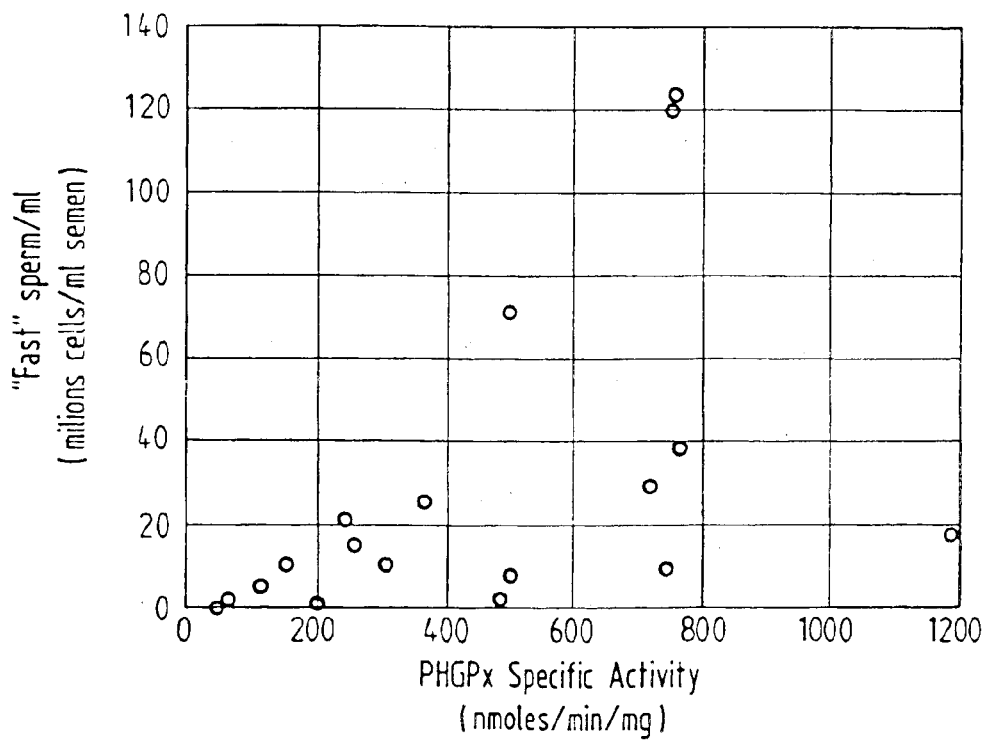

FIG. 6 shows the relationship between PHGPx specific activity and number of "fast" sperms per milliliter of semen. "Fast" is a parameter of sperm mobility.

TABLE 1

PHGPx activity in spermatogenic cells, spermatozoa and sperm capsule. Effect of thiols.

| Preparation mU/mg protein[a,b] | |
|---|---|
| Cells from seminiferous tubules | |
| 5 mM 2-mercaptoethanol[c] | 250 ± 10 |
| 100 mM 2-mercaptoethanol[c] | 260 ± 10 |
| Spermatozoa from tail of epididymis | |
| 5 mM 2-mercaptoethanol[c] | undetectable |
| 100 mM 2-mercaptoethanol[c] | 3,140 ± 200 |
| Mitochondrial capsule | |
| 5 mM 2-mercaptoethanol[c] | undetectable |
| 100 mM 2-mercaptoethanol[c] | 5,600 ± 290 |

[a]One enzyme mU catalyzes the reduction of one nanomole of phosphatidylcholine hydroperoxide per minute at 37° C. in the presence of 3 mM GSH.
[b]Data are the mean and S. D. of five independent measurements.
[c]Solubilisation/reduction was carried out in 0.1M Tris-HCl, 6M guanidine-HCl, 0.5 µg/ml pepstatin A, 0.7 µg/ml leupeptin and 2-mercaptoethanol as indicated at pH 7.5 and 4° C. for 10 min Low molecular weight compounds were removed before activity determination by a NAP 5 cartridge.

REFERENCES

1. Calvin, H. I., Cooper, G. W. & Wallace, E. Evidence that selenium in rat sperm is associated with a cysteine-rich structural protein of the mitochondrial capsules. *Gamete Res.* 4, 139–149 (1981).
2. Brown, D. G. & Burk, R. F. Selenium retention in tissues and sperm of rats fed a Torula yeast diet. *J. Nutr.* 103, 102–108 (1973).
3. Wu, A. S. H., Oldfield, J. E., Shull, L. R. & Cheeke, P. R. Specific effect of selenium deficiency on rat sperm. *Biol. Reprod.* 20, 793–798 (1979).
4. Wallace, E., Calvin, H. I., Ploetz, K. & Cooper, G.-W. Functional and developmental studies on the role of selenium in spermatogenesis. In: Combs, G. F., Levander, O. A., Spallholz, J. E., and Oldfield, J. E. (eds): *Selenium in Biology and Medicine*. AVI Publishing Co, Westport, Conn. Part A, 181–196 (1987).
5. Behne, D., Weiler, H. & Kyriakopoulos, A. Effects of selenium deficiency on testicular morphology and function in rats. *J. Reprod. Fertil.* 106, 291–297 (1996).
6. Maiorino, M. et al. Testosterone mediates expression of the selenoprotein PHGPx by induction of spermatogenesis and not by direct transcriptional gene activation. *FASEB J.* 12, 1359–1370 (1998).
7. Cataldo, L., Baig, K., Oko, R., Mastrangelo, M.-A. & Kleene, K. C. Developmental expression, intracellular localization, and selenium content of the cysteine-rich protein associated with the mitochondrial capsules of mouse sperm. *Mol. Reprod. Dev.* 45, 320–331 (1996).
8. Pallini, V. & Bacci, E. Bull sperm selenium is bound to a structural protein of mitochondria. *J. Submicr. Cytol.* 11, 165–170 (1979).
9. Nam, S.-Y., Youn, H.-Y., Ogawa, K., Kurohmaru, M. & Hayashi, Y. Expression of mitochondrial capsule selenoprotein mRNA increases with aging, but decreases by selenium deficiency in the mouse testis. *J. Reprod. Develop.t* 43, 227–234 (1997).
10. Adham, I. M. et al. Cloning, expression, and chromosomal localization of the rat mitochondrial capsule selenoprotein gene (MCS): the reading frame does not contain potential UGA selenocysteine codons. *DNA Cell Biol.* 15, 159–166 (1996).
11. Brigelius-Flohé, R. et al. Phospholipid-hydroperoxide glutathione peroxidase: genomic DNA, cDNA, and deduced amino acid sequence. *J. Diol. Chem.* 269, 7342–7348 (1994).
12. Pushpa-Rekha, T. R., Burdsall, A. L., Oleksa, L. M., Chisolm, G. M. & Driscoll, D. M. Rat phospholipid-hydroperoxide glutathione peroxidase. cDNA cloning and identification of multiple transcription and translation start sites. *J. Biol. Chem.* 270, 26993–26999 (1995).
13. Arai, M. et al. Import into mitochondria of phospholipid hydroperoxide glutathione peroxidase requires a leader sequence. *Biochem. Biophys. Res. Comm.* 227, 433–439 (1996).
14. Schuckelt, R. et al. Phospholipid hydroperoxidase glutathione peroxidase is a selenoenzyme distinct from the classical glutathione peroxidase as evident from cDNA and amino acid sequencing. *Free Rad. Res. Comm.* 14, 343–361 (1991).
15. Maiorino, M. et al. Probing the presumed catalytic triad of selenium-containing peroxidases by mutational analysis of phospholipid hydroperoxide glutathione peroxidase (PHGPx). *Biol. Chem. Hoppe Seyler* 376, 651–660 (1995).
16. Ursini, F. et al. The diversity of glutathione peroxidases. *Meth. Enzymol.* 252, 38–53 (1995).
17. Bauché, F., Fouchard, M.-H. & Jégou, B. Antioxidant system in rat testicular cells. *FEBS Lett.* 349, 392–396 (1994).
18. Shalgi, R., Seligman, J. & Kosower, N. S. Dynamics of the thiol status of rat spermatozoa during maturation: analysis with the fluorescent labeling agent monobromobimane. *Biol. Reprod.* 40, 1037–1045 (1989).
19. Seligman, J., Kosower, N. S. & Shalgi, R. Effects of caput ligation on rat sperm and epididymis: protein thiols and fertilizing ability. *Biol. Reprod.* 46, 301–308 (1992).
20. Fisher, H. M. & Aitken, R. J. Comparative analysis of the ability of precursor germ cells and epididymal spermatozoa to generate reactive oxygen metabolites. *J. Exp. Zool.* 277, 390–400 (1997).
21. Roveri, A. et al. Phospholipid hydroperoxide glutathione peroxidase of rat testis: Gonadotropin dependency and immunocytochemical identification. *J. Biol. Chem.* 267, 6142–6146 (1992).
22. Giannattasio, A., Girotti, M., Williams, K., Hall, L. & Bellastella, A. Puberty influences expression of phospholipid hydroperoxide glutathione peroxidase (GPx4) in rat testis: probable hypophysis regulation of the enzyme in male reproductive tract. *J. Endocrinol. Invest.* 20, 439–444 (1997).
23. Weitzel, F. & Wendel, A. Selenoenzymes regulate the activity of leukocyte 5-lipoxygenase via the peroxide tone. *J. Biol. Chem.* 268, 6288–6292 (1993).
24. Brigelius-Flohé, R., Friedrichs, B., Maurer, S., Schultz, M. & Streicher, R. IL-1 induced NFκB activation is inhibited by overexpression of PHGPx in a human endothelial cell line. *Biochem. J.* 328, 199–203 (1997).
25. Sandstrom, P. A., Murray, J., Folks, T. M. & Diamond, A. M. Antioxidant defenses influence HIV-1 replication and associated cytopathic effects. *Free Radic. Biol. Med.* 24, 1485–1491. (1998).
26. Li, L., Seddon, A. P., Meister, A. & Risley, M. S. Spermatogenic cell—somatic cell interaction are required for maintenance of spermatogenic cell glutathione. *Biol. Reprod.* 40, 317–331 (1989).
27. Gobom, J., Nordhoff, E., Ekman, R., Roepstorff, P. Rapid micro-scale proteolysis of proteins for MALDI-MS peptide mapping using immobilized trypsin. *Int. J. Mass Spectrom.* 169/170, 153–163 (1998).
28. Roveri, A., Maiorino, M. & Ursini, F. Enzymatic and immunological measurements of soluble and membrane bound PHGPx. *Meth. Enzymol.* 233, 202–212 (1994).
29. Flohé, L. Determination of glutathione peroxidase. In: CRC Handbook of Free radicals and Antioxidants in Biomedicine, Vol. III. J. Miquel, A. T. Quintanilha and H. Weber (eds.). CRC Press, Inc., Boca Raton/Fla., 281–286 (1988).
30. Brecht, A., Rothmund, M., Schütz, A., Schabel, U. Gauglitz, G. Optische Methoden im High-Throughoutput-Screening zur Wirkstoffsuche. *BioTec* 3, 26–28 (1998).

What is claimed is:

1. A method for determining the concentration of latent phospholipid hydroperoxide glutathione peroxidase (PHGPx) in a sperm sample, comprising the steps of:
   a. obtaining the sperm sample,
   b. solubilizing spermatozoa in said sperm sample by adding detergents and chaotropic agents;
   c. reactivating latent PHGPx by adding thiols;
   d. removing the chaotropic agents and thiols from the sample; and,
   e. determining the concentration of the latent PHGPx.

2. The method according to claim 1, wherein the chaotropic agents and thiols are removed by gel filtration.

3. The method according to claim 1, wherein the concentration of solubilized PHGPx is determined by immunological techniques or measurement of enzymatic activity of said solubilized PHGPx.

4. The method according to claim 1, wherein the chaotropic agent is 4–8 M guanidine chloride, 4–8 M guanidine thiocyanate or 5–8 M urea.

5. The method according to claim 1, wherein the thiol is 50–300 mM 2-mercaptoethanol, 25–300 mM dithiothreitol (DTT) or dithioerythritol (DTE).

6. The method according to claim 1, wherein the sperm sample is from humans or livestock.

7. The method according to claim 1, comprising the step of calculating fertilizing potential of said spermatozoa by using the concentration of latent PHGPx.

\* \* \* \* \*